United States Patent [19]

Dirlam et al.

[11] Patent Number: 5,403,738
[45] Date of Patent: Apr. 4, 1995

[54] MICROORGANISM FOR PRODUCING POLYCYCLIC ETHER ANTIBIOTICS

[75] Inventors: John P. Dirlam, Gales Ferry; Walter P. Cullen, East Lyme, both of Conn.; Hiroshi Maeda; Junsuke Tone, both of Chita, Japan

[73] Assignee: Pfizer Inc., New York, N.Y.

[21] Appl. No.: 169,566

[22] Filed: Dec. 17, 1993

Related U.S. Application Data

[62] Division of Ser. No. 655,440, Mar. 27, 1992, Pat. No. 5,298,524.

[51] Int. Cl.$^6$ ............................................. C12N 1/20
[52] U.S. Cl. ................................. 435/252.1; 435/825; 435/118; 435/119
[58] Field of Search ..................... 435/252.1, 119, 822, 435/118, 117, 825, 170

[56] References Cited

U.S. PATENT DOCUMENTS

| | | | |
|---|---|---|---|
| 4,148,882 | 4/1979 | Celmer et al. | 424/122 |
| 4,195,079 | 5/1980 | Celmer et al. | 424/122 |
| 4,431,665 | 2/1984 | Kluge et al. | 549/343 |
| 4,504,584 | 3/1985 | Kitaura et al. | 435/253 |
| 4,582,822 | 4/1986 | Hamill et al. | 514/25 |
| 5,147,858 | 9/1992 | Dirlam | 514/23 |

FOREIGN PATENT DOCUMENTS

| | | |
|---|---|---|
| 156193 | 10/1985 | European Pat. Off. . |
| 169011 | 1/1986 | European Pat. Off. . |

OTHER PUBLICATIONS

Miyadoh et al., *Int. J. Syst. Bacteriol.*, 1987, vol. 37, pp. 342–346.

Kroppensted et al. In "The Prokaryotes" Balows et al., ed., vol. II 1992, pp. 1096–1099, Springer-Verlag.

Tsou et al., J. Antibiotics (Japan), 37, 1651–63 (1984).

Labeda et al., Intl. J. Systematic Bacteriol. 35, 333–336 (1985).

Perry's Chem. Engineer's Handbook, 6th Ed., McGraw-Hill Book Co., N.Y., 1984, pp. 27-1 to 27-14.

Tone et al., Current Chemotherapy and Infectious Diseases, Proc. 11th ICC and 19th ICAAC, Am. Soc. Microbiol., 1980, pp. 469–470.

Tone et al., Program and Abstracts of the 21st Interscience Conference on Antimicrobial Agents and Chemotherapy, 1981, Abstr. No. 186.

Dobashi et al., J. Antibiotics (Japan), 42, 629, 632 (1989).

*Primary Examiner*—Irene Marx
*Attorney, Agent, or Firm*—Peter C. Richardson; Gregg C. Benson; Robert T. Ronau

[57] ABSTRACT

An acidic polycyclic ether antibiotic, having structure established by X-ray crystallography, is formed by fermentation of a novel microorganism, Actinomadura sp. ATCC 53764. This novel antibiotic is useful as an anticoccidial in chickens, in the prevention or treatment of swine dysentery, and as a growth promotant in cattle and swine.

3 Claims, No Drawings

MICROORGANISM FOR PRODUCING POLYCYCLIC ETHER ANTIBIOTICS

This is a division of application Ser. No. 07/655,440, filed on Mar. 27, 1992, now U.S. Pat. No. 5,298,524, entitled ACIDIC POLYCYCLIC ETHER ANTIBIOTIC HAVING ANTICOCCIDIAL AND GROWTH PROMOTANT ACTIVITY.

BACKGROUND OF THE INVENTION

The present invention concerns a new acidic polycyclic ether antibiotic having the formula:

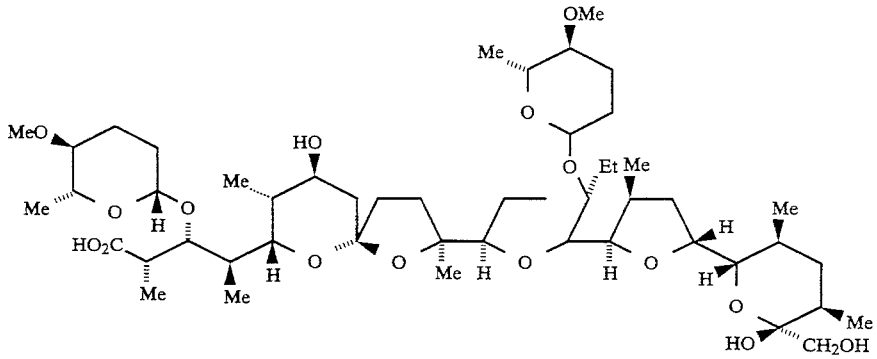

wherein Me=methyl and Et=ethyl, having relative stereochemistry as shown; pharmaceutically acceptable cationic salts thereof; nutrient feed compositions comprising said antibiotic for poultry, cattle or swine; its use as an anticoccidial agent in poultry, in the treatment or prevention of swine dysentery, or as a growth promotant in cattle or swine; a fermentation method for its preparation; and the Actinomadura sp. microorganism which produces said antibiotic in said fermentation method.

The compound (I) is a new member of the acidic polycyclic ether group of antibiotics. This family includes such well known agents as monensin (The Merck Index, 10th Ed., Merck and Co.,Inc., Rahway, N.J., 1983, monograph no. 6100), nigericin (loc. cit., monograph no. 6390), narasin (loc. cit., monograph no. 6271), lasalocid (loc. cit., monograph no. 5204), and salinomycin (loc. cit., monograph no. 8193). The subject has been reviewed by Westley, "Polyether Antibiotics", Adv. Appl. Microbiol., vol. 22, pp. 177–223 (1977). These compounds are generally known as coccidiostats, as feed additive-growth promotants, and/or as agents useful against swine dysentery.

SUMMARY OF THE INVENTION

A culture of Actinomadura sp., ATCC 53764, when fermented under aerobic conditions in aqueous media, produces a new acidic polycyclic ether antibiotic, a compound having the formula (I), as specified above.

The present invention is directed to said compound of the formula (I), including the pharmaceutically-acceptable cationic salts thereof, and to a process for its preparation which comprises fermentation of said Actinomadura sp. ATCC 53764 in an aqueous nutrient medium comprising an assimilable source of carbon and nitrogen until a recoverable amount of said compound of the formula (I) is formed, preferably under submerged aerobic conditions. For use as an anticoccidial agent, in the prevention or treatment of swine dysentery, and/or as a growth promotant, the compound (I) is not necessarily separated from the fermentation and isolated in substantially pure form, but is alternatively used in crude form, either in precipitated form admixed with mycelium (recovered by filtration of the fermentation medium), or in solids obtained by spray- or freeze-drying the entire fermentation medium.

Said pharmaceutically-acceptable cationic salts include, but are not limited to, those of sodium, potassium, calcium, ammonia, N,N'-dibenzylethylenediamine, N-methylglucamine (meglumine) and diethanolamine. The preferred cationic salts are those of potassium and sodium.

The present invention is also directed to nutrient feed compositions, one for cattle or swine which comprises the compound of the formula (I) in an amount effective to promote growth and/or improve the feed utilization of said cattle or swine, or to prevent or treat dysentery in swine; and the other for poultry which comprises the compound of the formula (I) in an amount effective to control coccidial infection in said poultry.

The present invention is further directed to a method for promoting growth and/or increasing the efficiency of feed utilization in swine or cattle which comprises administering to said swine or cattle a growth promoting or feed-utilization efficiency promoting amount of the compound of the formula (I), particularly in the form of a nutrient feed composition; to a method for preventing or treating dysentery in swine which comprises administering to said swine a compound of the formula (I) in an amount effective in preventing or treating said dysentery in said swine; and to a method for controlling coccidial infections in poultry which comprises administering to said poultry an anticoccidially effective amount of the compound of the formula (I), particularly in the form of a nutrient feed composition.

Finally, the present invention is directed to a biologically pure culture of Actinomadura sp. ATCC 53764, said culture being capable of producing the compound of the formula (I) in a recoverable quantity upon fermentation in an aqueous nutrient medium comprising assimilable sources of carbon and nitrogen; including said culture in freeze-dried form.

DETAILED DESCRIPTION OF THE INVENTION

The culture capable of producing the present polycyclic ether antibiotic of the formula (I) is designated Actinomadura sp., and was deposited Apr. 13, 1988 under the Budapest treaty in The American Type Culture Collection, Rockville, Maryland as the type culture under their accession number ATCC 53764. Permanency of the deposit of this culture at The American Type Culture Collection at Rockville, Maryland and ready accessibility thereto by the public are afforded throughout the effective life of the patent in the event the patent is granted. Access to the culture is available during pendency of the application under 37 CFR 1.14 and 35 USC 122. All restrictions on the availability to the public of the culture deposited will be irrevocably removed upon granting of the patent.

This novel culture was derived from a soil sample collected in Nigeria, and identified in the culture collection of Pfizer Inc. as N762-11. Its description and classification were provided by Dr. L. H. Huang. This culture was found to produce narrow dimensions of the hyphae typical of the actinomycetes, an aerial mycelium upon which short spore chains are produced, and an unfragmented substrate mycelium. The results of the whole cell analyses further indicate that it belongs to the genus Actinomadura.

A slant culture of the microorganism on ATCC 172 media was inoculated into ATCC 172 broth and grown for four days at 28° C. on a shaker. It was then centrifuged for 20 minutes, washed three times with sterile distilled water, and planted on media commonly used for identification of members of the Actinomycetales.

The cultures were incubated at 28° C. and the results read at varying times, but most commonly at fourteen days. The colors were described in common. terminology, but exact colors were determined by comparisons with color chips from *The Color Harmony Manual*, fourth edition. The methods of whole-cell amino acid and sugar analyses are those described in Becker et al., Appl. Microbiol., vol. 12, pp. 421–423 (1964), and in Lechevalier, J. Lab. Clin. Med., Vol. 71, pp. 934–944 (1968), respectively.

The culture was identified as follows:

Yeast Extract-Malt Extract Agar (ISP #2 medium, Difco)—Growth poor to moderate; white, cream to gray (2 ca, near gray series 3 ih, 3 ml); raised, wrinkled, or appearing as isolated colonies, aerial mycelium white to gray (near gray series 3 ih, 3 ml); reverse yellowish gray to gray (2 ie, 2 ig, near gray series 3 ih); soluble pigment yellowish gray (2 ie).

Oatmeal Agar (ISP #3 medium, Difco)—Growth moderate, white to cream (2 ca), slightly raised, smooth, with white aerial mycelium; reverse cream (2 ca); soluble pigment cream (2 ca).

Inorganic Salts-Starch Agar (ISP #4 medium, Difco)—Growth moderate, white, slightly raised, smooth with white aerial mycelium; reverse colorless to cream (2 ca); no soluble pigment.

Glycerol-Asparagine Agar (ISP #5 medium, Difco)—Growth poor to moderate, white, slightly raised, smooth to granular, aerial mycelium white; reverse colorless; no soluble pigment.

Czapek-Sucrose Agar (Waksman, "The Actinomycetes", v. 2, medium #1, p. 328, 1961)—Growth moderate to good, white to cream (2 ca), slightly raised, smooth, aerial mycelium white; reverse colorless to cream (2 ca); no soluble pigment.

Glucose-Asparagine Agar (ibid. , medium #2)—Growth poor, white to cream (2 ca), thin to slightly raised, smooth to granular, aerial mycelium white; reverse colorless, cream to pale yellowish (2 ca, 2 ea); no soluble pigment.

Gordon and Smith's Tyrosine Agar (Gordon and Smith, J. Bacteriol., 69:147-150, 1955)—Growth good, dark pink (4 gc), moderately raised, smooth, no aerial mycelium; reverse pale yellowish brown (3 gc); soluble pigment brown (4 ng) .

Calcium Malate Agar (Waksman, Bacteriol. Rev., 21, 1–29, 1957)—Growth poor, cream (2 ca), thin, smooth to slightly granular; aerial mycelium sparse, white; reverse colorless to cream (2 ca); no soluble pigment.

Casein Agar (Gordon and Smith, ibid.)—No growth. But after four weeks of incubation, growth poor, dark cream (near 2 gc), moderately raised, wrinkled, aerial mycelium white; reverse grayish yellow (2 le); soluble pigment grayish (2 ig) .

Bennett's Agar. (Waksman, loc. cit., medium #30, p. 331)—Growth good, gray (near gray series 3 fe, 3 ih) with some white dots, raised, wrinkled, aerial mycelium white to gray (near gray series 3 fe, 3 ih); reverse grayish black (near gray series 3 ih, 3 ml); soluble pigment yellowish gray (2 ig).

Emerson's Agar (ibid., medium #28, p. 331)—Growth poor to moderate, cream, pale yellowish, yellowish gray to dark gray (2 ca, 2 ea, 2 ia, near gray series 3 ih, 3 ml); raised, wrinkled to granular, aerial mycelium gray (near gray series 3 ih); reverse yellowish to gray (near gray series 2 ih); soluble pigment yellowish gray (2 le, 2 ie).

Nutrient Agar (ibid., medium #14, p. 330)—Growth moderate, pale yellowish to yellowish (2 ea, 2 ga) slightly raised, smooth, no aerial mycelium; reverse same as surface; no soluble pigment.

Gelatin Agar (Gordon and Mihm, J. Bacteriol., 73, 15–27, 1957)—Growth moderate to good, whitish orange to yellowish orange (3 ea, 3 ia, 4 ea), moderately raised, smooth but wrinkled near edge, no aerial mycelium; reverse yellowish orange (3 ia); no soluble pigment.

Starch Agar (ibid.)—Growth moderate to good, whitish orange to yellowish orange (3 ea, 3 ia), moderately raised, smooth, no aerial mycelium; reverse yellowish orange (3 ia); no soluble pigment.

Potato Carrot Agar (Lechevalier, Lab. Clin. Med., 71, 934-944, 1968, but use only 30 g. potatoes, 2.5 g. carrots and 20 g. agar)—Growth moderate, cream (2 ca), thin, smooth; no aerial mycelium; reverse cream (2 ca); no soluble pigment.

Tap Water Agar (2%)—Growth poor to moderate, white, thin, smooth; aerial mycelium white; reverse colorless to cream (2 ca); no soluble pigment.

Gauze's Mineral Medium 1 (Gauze et al., Problems in the Classification of Antagonistic Actinomycetes, English Ed., p. 13, 1957)—Growth moderate to good, white to cream (2 ca), slightly raised, smooth; aerial mycelium white; reverse cream (2 ca); no soluble pigment.

Gauze's Organic Medium 2 (ibid.)—Growth moderate to good, cream to pale yellowish (2 ca, 2 ea), moderately raised, smooth to wrinkled, aerial mycelium none to sparse, white; reverse same as surface; no soluble pigment.

Morphological Properties—The morphological properties were observed after three weeks of incubation on Gauze's mineral medium 1: aerial mycelium white; spore chains short, flexuous, curved, hooked, or hooked to looped, occasionally coiling into a mass or with open coils of up to 1.5 to 2 turns; 3 to 9 spores per spore chain; oval to elliptical, sometimes globose, 0.7–1.0 micron diameter or 1.2–1.8×0.7–1.0 microns; spores warty, as revealed by scanning electron microscopy.

Biochemical Properties—Melanin not produced; hydrogen sulfide not produced; gelatin liquefied; starch not hydrolyzed; organic nitrate but not dextrose nitrate reduced to nitrite; poor growth but no decomposition on either Jensen's or Levine and Schoenlein's cellulose broth; no coagulation and no peptonization of milk; casein digestion positive. Carbohydrate utilization: glucose, sucrose, ribose and starch utilized; inositol, galactose, glycerol, melezitose, and trehalose doubtfully utilized; arabinose, fructose, mannitol, raffinose, rhamnose, xylose, adonitol, cellobiose, dulcitol, erythritol, lactose, maltose, mannose, melibiose, alpha-methyl-D-glucoside, salicin, sorbitol, and sorbose not utilized.

Acid production: acid produced from glucose, arabinose, fructose, mannitol, raffinose, rhamnose, sucrose, xylose, cellobiose, dulcitol, erythritol, lactose, maltose, mannose, melezitose, melibiose, ribose, salicin, sorbitol, sorbose, starch, and trehalose; acid not produced from inositol, adonitol, galactose, glycerol, and alpha-methyl-D-glucoside.

The other positive tests included utilization of acetate, citrate, pyruvate, and succinate; and decomposition of hypoxanthine. The following tests were negative: utilization of benzoate, dextrin, lactate, malate, mucate, oxalate, phenol, and propionate; decomposition of adenine and xanthine; and hydrolysis of hippurate, esculin, and urea; resistance to lysozyme.

| Temperature Relations | | | |
| --- | --- | --- | --- |
| 21° C. | 28° C. | 37° C. | 45° C. |
| Scant to Poor Growth | Good Growth | Good Growth | No Growth |

Whole-Cell Analysis—The whole-cell hydrolysates contained meso-diaminopimelic acid, glucose, galactose, madurose and ribose.

The culture N762-11 is characterized by the white to cream substrate mycelium; the short, colorless aerial (sometimes gray) colonies; the short spore chains which are flexuous, curved, hooked or looped; and the spores with a warty surface. The colors of the substrate mycelium might range from colorless, cream, pale yellowish, yellowish, yellowish orange, yellowish gray to gray. Among all of the sugars tested, only glucose, sucrose, ribose, and starch were utilized. Hypoxanthine (but not adenine and xanthine) was decomposed. The culture did not produce melanin and hydrogen sulfide; did not hydrolyze esculin, hippurate, starch, and urea; and was sensitive to lysozyme. The whole-cell hydrolysates contained meso-diaminopimelic acid and the diagnostic sugar madurose. Thus, the culture N762-11belongs in the genus Actinomadura, as defined by H. Lechevalier.

The culture N762-11 shows some similarity to the following known species of Actinomadura in cultural properties and/or biochemical properties: *A. atramentaria, A. livida,* and *A. macra*. It differs from *A. atramentaria* in the warty rather than smooth spores, the absence of dark brown substrate mycelium, the utilization of sucrose, the failure to produce melanin and to peptonize milk, and the ability to liquefy gelatin. Compared with *A. livida*, it differs in the white rather than cream aerial mycelium and the absence of the brown substrate mycelium.

The culture N762-11 differs from *Actinomadura macra* in the presence of hooked or looped spore chains, the warty rather than smooth spores, the ability to digest casein, the failure to produce hydrogen sulfide, and the utilization of ribose and starch.

On the basis of the data presented above, the culture N762-11 is considered as a member of the genus Actinomadura and designated Actinomadura sp. It has been deposited at the American Type Culture Collection under the accession number ATCC 53764.

The antibiotic compound (I) of the present invention is readily produced by the present Actinomadura sp. by growing at from about 24° to about 36° C. under submerged conditions with agitation and aeration on media consisting of carbohydrate sources such as sugars, starches, glycerol; organic nitrogen substances such as soybean meal, casamino acids, yeast extract; growth substances such as grain solubles, fish meal, cotton seed meal; mineral salts containing trace elements such as iron, cobalt, copper, zinc, etc. and calcium carbonate or phosphates as buffering agents. After growth has been completed, the antibiotic is readily recovered by extracting the whole broth with an organic solvent such as n-butanol, methylisobutyl ketone, or chloroform at pH ranges from 4.0 to 8.0; by filtering off the mycelium, which contains the precipitated antibiotic, the filtrate being discarded; or by simply spray-drying or freeze-drying the whole broth. Alternatively, the mycelium or the whole dried broth is extracted with one of said organic solvents. The purified antibiotic compound, if that is desired, is isolated from the organic extract by standard methods of concentration, salt or free acid formation, chromatography, precipitation and/or crystallization, as exemplified below.

In the usual manner of carrying out the fermentation, an inoculum is first prepared by scraping vegetative cells, growing on a suitable media, from slants or Roux bottles which have been inoculated with Actinomadura sp. ATCC 53764. The resulting vegetative cells are in turn used to inoculate shake flasks or inoculum tanks, also containing suitable growth media. Alternatively, the inoculum tanks are inoculated from the shake flasks. Following a suitable growth period (generally 120 to 144 hours in shake flasks and 168 to 196 hours in inoculum tanks), a fermenter, also containing suitable growth media, is inoculated under aseptic conditions with vegetative broth from the shake flasks or inoculum tanks. Upon completion of growth (generally about 120–196 hours), the antibiotic compound is recovered in crude or pure form, as desired, by one or another of the methods generally described above, or by specific methods which are exemplified below.

The compound of the formula (I) is tested for in vitro antibacterial activity by standard methods in which the minimum inhibitory concentrations (MIC's) in mcg/ml against one or more microorganisms is measured. One such procedure is the one recommended by the International Collaborative Study on Antibiotic Sensitivity Testing (Ericcson and Sherris, *Acta. Pathologica et Microbiologia Scandinav*, Supp. 217, Section B: 64–68 [1971]), and employs brain heart infusion (BHI) agar and an inocula replicating device. Overnight growth tubes are diluted 100 fold for use as the standard inoculum (20,000–100,000 cells in approximately 0.002 ml. are placed on the agar surface; 20 ml. of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye. Like other polycyclic ether antibiotics, the present compound of the formula (I) typically shows Gram positive antibacterial activity, as well as activity against *Treponema hyodysenteriae*, (the causative agent of swine dysentery) as illustrated in Table I.

TABLE I

IN VITRO ANTIBACTERIAL ACTIVITY OF THE COMPOUND OF THE FORMULA (I)

| Organism | Strain No. | MIC, mcg/ml |
| --- | --- | --- |
| *Clostridium perfringens* | 10A009 | 100 |
| *Actinomyces pyogenes* | 14D002 | 50 |
| *Treponema hyodysenteriae* | 94A001 | 0.78 |

Efficacy data for the compound of the formula (I) and its salts against coccidial infections in chickens is obtained by the following method. Groups of 3–5 ten-day old pathogen free white leghorn cockerel chicks are fed a mash diet containing the compound (I) or its sodium and/or potassium salt uniformly dispersed therein. After being on this ration for 24 hours each chick is inoculated per os with oocysts of the particular species of Eimeria being tested. Other groups of 3–5 ten-day old chicks are fed a similar mash diet without compound (I) or its salts. They are also infected after 24 hours and serve as infected controls. Yet another group of 3–5 ten-day old chicks are fed the same mash diet without antibiotic and are not infected with coccidia. These served as normal controls. The results of treatment are evaluated after five days in the case of *E. acervulina*, and six days for all other challenges.

The criteria used to measure anticoccidial activity consists of lesion scores of 0 to 4 for *E. tenella* after J. E. Lynch, "A New Method of the Primary Evaluation of Anticoccidial Activity", *Am. J. Vet. Res.*, 22,324–326, 1961; and 0 to 3 for the other species based on modification of the scoring system devised by J. Johnson and W. H. Reid, "Anticoccidial Drugs. Lesion Scoring Techniques in Battery and Floor Pen Experiments in Chicks", *Exp. Parasit.*, 28, 30–36, 1970. Activity is measured by dividing the lesion score of each treated group by the lesion score of the infected control. In this test, the compound (I) and its cationic salts exhibit exceptionally high activity against *Eimeria tenella, E. acervulina, E. maxima*, and *E. necatrix* infections in poultry when incorporated into the mash diet of chickens at levels of about 1.0 to 20 ppm. For example, the compound of the formula (I) was some 6 to 24 times more effective than salinomycin when compared by this test method.

The present compound of the formula (I) is also generally useful in combination with certain other known anticoccidial agents, such as nicarbazin, 4,4'-dinitrocarbanilide or a naphthalenamine, as defined by Hamill et al., U.S. Pat. No. 4,582,822, cited above.

For the prevention or control of coccidiosis in poultry, the compound of this invention is orally administered to poultry in a suitable carrier. Conveniently, the medication is simply carried in the drinking water or in the poultry feed, so that a therapeutic dosage of the agent is ingested with the daily water or poultry ration. The agent can be directly metered into drinking water, preferably in the form of a liquid concentrate, or added directly to the feed as such, or in the form of a premix or concentrate. A premix or concentrate of therapeutic agent in a carrier is commonly employed for the inclusion of the agent in the feed. The therapeutic agent can be in substantially pure form (e.g., the free acid, or a pharmaceutically-acceptable salt thereof), in assayed crude form such as wet or dry mycelium or dried whole broth. Suitable carriers are liquid or solid, as desired, such as water, various meals (for example, soybean oil meal, linseed oil meal, corncob meal) and mineral mixes such as are commonly employed in poultry feeds. A particularly effective carrier is the poultry feed itself; that is, a small portion of poultry feed. The carrier facilitates uniform distribution of the active materials in the finished feed with which the premix is blended. This is important because only small proportions of the present potent agents are required. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates are blended by the feed manufacturer with proteinaceous carrier such as soybean oil meal and other meals, as described above, to produce concentrated supplements which are suitable for direct feeding to poultry. In such instances, the poultry are permitted to consume the usual diet. Alternatively, such concentrated supplements are added directly to the poultry feed to produce a nutritionally balanced, finished feed containing a therapeutically effective level of one or more of the compounds of this invention. The mixtures are thoroughly blended by standard procedures, such as in a twin shell blender, to ensure homogeneity.

For use in poultry, the use levels of the compound described herein will vary under different circumstances. Continuous low-level medication, during the growing period; that is, during the first 5 to 12 weeks for chickens, is an effective prophylatic measure. In the treatment of established infections, higher levels may be necessary to overcome the infection. The use level of the compound (I) in feed will generally be in the range of about 1.0 to 25 ppm, preferably in the range of about 2.5 to 12.5 ppm. When administered in drinking water, the level which will be that which will provide the same daily dose of medication factored by the weight ratio of the average daily consumption of feed to the average daily consumption of water.

The activity of the compound of the formula (I) and its salts in the promotion of growth and/or increasing the efficiency of food utilization in swine or cattle can be measured directly by feeding test groups of animals various levels of the compound (I) or a salt in feed. Alternatively, British Patent Specification No. 1,197,826 details an in vitro rumen method for the evaluation of antibiotics in feeds.

For use in the prevention or treatment of swine dysentery, or in promoting growth and/or increasing the efficiency of feed utilization in cattle or swine the compound of the formula (I) or a salt is preferably administered as a feed additive. The feeds prepared according to methods fully analogous to those detailed above for the preparation of poultry feed, with the same concern for producing feeds in which the therapeutic agent is uniformly dispersed. The use level of the compound (I)

in cattle or swine feed will generally be in the range of about 0.25 to 25 ppm. In ruminants the compound of the formula (I) can also be orally administered in the form of a bolus which is retained in the rumenoreticular sac, releasing the therapeutic agent at a substantially constant rate over a prolonged period of time, e.g., 4–8 weeks, providing a dose equivalent to that of the above daily dose in feed, i.e.:

$$\text{average daily dose in milligrams} = (0.25 \text{ to } 25) \text{ ppm} \times \text{average daily feed consumption in Kg.}$$

Exemplary of such a controlled release bolus is that of Cardinal, U.S. Pat. No. 4,601,893.

The present invention is illustrated by the following examples. However, it should be understood that the invention is not limited to the specific details of these examples.

EXAMPLE 1

Fermentation of Actinomadura sp. ATCC 53764 Isolation of the Antibiotic of the Formula (I)

The Actinomadrua sp. was initially grown by inoculating solid media on slants or Roux bottles with the ATCC 53764 culture, using ATCC medium No. 172, prepared and having composition as follows.

|  | Grams/liter |
| --- | --- |
| Glucose | 10 |
| Soluble Starch | 20 |
| Yeast Extract | 5 |
| Casein Enzymatic Hydrolysate | 1 |
| Calcium Carbonate | 1 |
| Distilled Water to 1000 ml; pH to 7.0 with KOH; Add Agar | 20 |

Meanwhile, 300 ml shake flasks were prepared using in each flask 100 ml of one or the other of the following media:

| C' | Grams/liter | JDYTT | Grams/liter |
| --- | --- | --- | --- |
| Cerelose | 10 | Cerelose | 10 |
| Soy Flour | 10 | Corn Starch | 5 |
| Corn Fermentation Solids | 5 | Corn Steep Liquor | 5 |
| Corn Starch | 10 | Casein Enzymatic Hydrolysate | 5 |
| Sodium Chloride | 5 | Cobalt Chloride | 0.002 |
| Cobalt Chloride | 0.002 | Calcium Carbonate | 3 |
| Calcium Carbonate | 1 |  |  |

The medium-containing shake flasks were then sterilized at 120° C. and 15 p.s.i. for 30 minutes. After cooling, the medium was inoculated with a vegetative cell suspension scraped from the above Actinomadura sp. slant culture. The flasks were shaken at 28° C. on a shaker having a displacement of 1.5 to 2.5 inches at 150 to 200 cycles per minute (CPM) for five to seven days.

Meanwhile, 5 liter fermentation vessels were prepared containing 3 liters of one of the above C' or JDYTT media or the following media:

| UK1-2 | Grams/liter |
| --- | --- |
| Cerelose | 45 |
| Soy Flour | 10 |
| Corn Steep Liquor | 10 |
| Cobalt Chloride | 0.002 |
| Magnesium Sulfate | 0.10 |
| Calcium Carbonate | 3 |
| Manganese Sulfate | 0.10 |
| Ferric Sulfate | 0.10 |

An antifoaming agent (polypropyleneglycol, P2000, containing 10% ethylene oxide by weight, 1 ml) was added, and the vessels were sealed and sterilized at 120° C. and 15 p.s.i. for 45 minutes. The vessels were then inoculated with one shake flask (ca 3% inoculum), and fermented for 120 to 168 hours at 30° C., stirring at 1700 revolutions per minute (RPM) with an air rate of one volume of air per volume of liquid per minute.

When the fermentation was completed (based on an antibiotic disc assay versus *B. subtilis* ATCC 6633) the fermenters were stopped and filtered at the natural pH with the aid of a diatomaceous earth. The filter cake was slurried in methanol, concentrated in vacuo, diluted with 2–3 volumes of water then extracted 2X with ⅓ to ½ volume of either methylisobutyl ketone or n-butanol. The solvent layer was separated from the aqueous phase by aspiration or centrifugation, sparkled and concentrated in vacuo to yield the antibiotic of the formula (I) in crude form as a viscous oil.

The bioactivity of the broth and subsequent recovery streams can be followed by using a sensitive strain of *Bacillus subtilis* ATCC 6633 or *Staphylococcus aureus* ATCC 6538. The components in the broth and recovery streams can be visualized by thin layer chromatography (tlc) using Analtech silica gel GF plates employing ethyl acetate as eluant. The developed plates are sprayed with vanillin reagent (3 g vanillin in 75 ml ethanol and 25 ml 85% phosphoric acid) and heated to 80° C. The antibiotic product of the formula (I) appears as an orange spot. The developed tlc plate can also be overlayed with agar seeded with either *S. aureus* or *B. subtilis* to which 2,3,5-triphenyl-2H-tetrazolium chloride monohydrate has been added and incubated at 37° C. for 16 hours to visualize the antibiotic (white spots against a pink background).

Scale-up in large fermentation vessels was carried out by preparing shake flasks containing 0.7 liters of C' or JDYTT medium. The shake flask inoculum was fermented for 5 to 7 days at 28° C., and used to inoculate a 200 or a 4000 liter fermentation vessel containing 100 or 4000 liters of UK1-2 medium, respectively. Approximately one liter of inoculum was used in each tank. The fermentations, after proceeding for 7 to 10 days, were harvested.

The whole broth of the smaller fermentation run was extracted with 33 liters of methylisobutyl ketone at natural pH. The organic extract was separated on an alpha-DeLaval separator and concentrated under vacuum to yield the crude antibiotic of the formula I as an oil.

Work-up of the large tank fermentation was carried out by extracting the approximately 4000 liters of whole broth with 1400 liters of methylisobutyl ketone. The organic extract was separated and concentrated under vacuum, initially in a vacuum pan and finally on a rotary evaporator to yield 12 liters of crude product as a syrup. The syrup was extracted 2×25 liters of methanol. The extracts were combined and restripped to a second oil which was chromatographed on Sephadex LH20, monitored by tlc as described above. Product containing cuts were combined and chromatographed on silica gel, eluted sequentially with hexane, toluene, CHCl$_3$, ethyl acetate and acetone, again monitoring by tlc. The desired product was contained in the CHCl$_3$ and ethyl acetate cuts. The latter were combined, concentrated to 85 g of residue and rechromatographed in silica gel using 1:1 ethyl acetate: hexane as eluant. Product fractions were combined, treated with activated carbon, filtered, shaken with pH 9.0 dibasic sodium phosphate buffer from the sodium salt, dried over Na$_2$SO$_4$, stripped and the 2.03 g of antibiotic of the formula (I) recovered as the sodium salt.

In a second 4000 liter fermentation the initial crude syrup was extracted 2×25 liters of 1:3 methanol: hexane, the extracts combined and stripped to an oil. The latter was chromatographed on 3 Kg of silica gel, initially eluting with hexane, then ethyl acetate and finally 9:1 ethyl acetate: acetone. Product containing fractions, identified by tlc, were combined, stripped, taken up in ethyl acetate, treated with activated carbon, filtered, and extracted with dilute phosphoric acid and then with pH 9.0 phosphate buffer. The organic phase was dried (Na$_2$SO$_4$), stripped, and the residue crystallized by trituration with heptane and dried under high vacuum to yield 2.2 g of the antibiotic of the formula (I) in the form of its sodium salt; mp 265°–267° C.; [alpha]$_D^{25}$ = +31.2° (c = 1, CHCl$_3$).

Anal. Calcd. for C$_{50}$H$_{85}$O$_{16}$Na.2H$_2$O: C, 59.98; H, 8.95 Found: C, 59.61; H, 8.56.

EXAMPLE 2

Compound (I) in the Free Acid Form

The free acid form of the antibiotic of the formula (I) was prepared by vigorously shaking a chloroform solution of the sodium salt with an equal volume of hydrochloric acid at pH 2 in a separatory funnel. The phases were separated, and the chloroform layer was washed with water and then evaporated under vacuum to give the free acid: mp 115°–117° C.; [alpha]$_D^{25}$ = +21.6° (c = 1, CHCl$_3$)

Anal. Calcd for C$_{50}$H$_{86}$O$_{16}$: C, 63.67; H, 9.19 Found: C, 63.52; H, 9.36.

C-13 nmr (chemical shift (ppm) in CDCl$_3$ with number of hydrogens in parentheses): 177.0 (0), 107.7 (0), 101.5 (1), 97.6 (1), 96.9 (0), 89.2 (0), 85.5 (0), 84.9 (1), 84.4 (1), 82.4 (1), 80.5 (1), 80.4 (1), 76.7 (1), 75.1 (1), 74.8 (1), 74.6 (1), 73.9 (1), 71.0 (1), 68.1 (2), 67.2 (1), 56.9 (3), 56.8 (3), 41.3 (1), 38.5 (2), 37.5 (1), 36.6 (2), 36.0 (1), 34.8 (1), 34.6 (1), 34.0 (2), 33.6 (2), 32.8 (1), 32.8 (2), 30.8 (2), 30.8 (2), 27.8 (3), 27.6 (2), 27.4 (2), 27.3 (2), 26.6 (2), 24.4 (2), 18.3 (3), 18.3 (3), 17.4 (3), 16.2 (3), 16.0 (3), 15.5 (3), 10.7 (3), 10.6 (3), and 10.1 (3).

The free acid was recrystallized by slow evaporation from diethyl ether and the X-ray structure was determined on the resulting crystals by Dr. J. Bordner.

EXAMPLE 3

The Sodium Salt of the Compound (I)

The free acid of the preceding Example (130 mg) was dissolved in 100 ml of chloroform. A solution of sodium carbonate (0.3 g) in water (100 ml) was added and the resulting mixture was then placed in a separatory funnel and vigorously shaken for several minutes. The chloroform layer was separated, washed with water, dried over sodium sulfate, filtered, and evaporated to afford 136 mg of the sodium salt; having mp and other properties identical to the sodium salt described above.

EXAMPLE 4

The Potassium Salt of the Compound (I)

To prepare the potassium salt of the antibiotic compound of the formula (I), the free acid (120 mg) was dissolved in 100 ml of chloroform. K$_2$CO$_3$ (0.5 g) in 100 ml of H$_2$O was added and the resulting mixture stirred for several minutes, then placed in a separatory funnel and vigorously shaken for several minutes. The organic phase was separated, washed with water and evaporated under vacuum to afford title product; mp 130°–135° C., [alpha]$_D^{25}$ = +22.8° (c = 1, chloroform).

Anal. Calcd. for C$_{50}$H$_{85}$O$_{16}$K: C, 61.14; H, 8.66. Found: C, 61.89; H, 8.98.

We claim:

1. A biologically pure culture of Actinomadura sp. ATCC 53764 which produces the compound of the formula

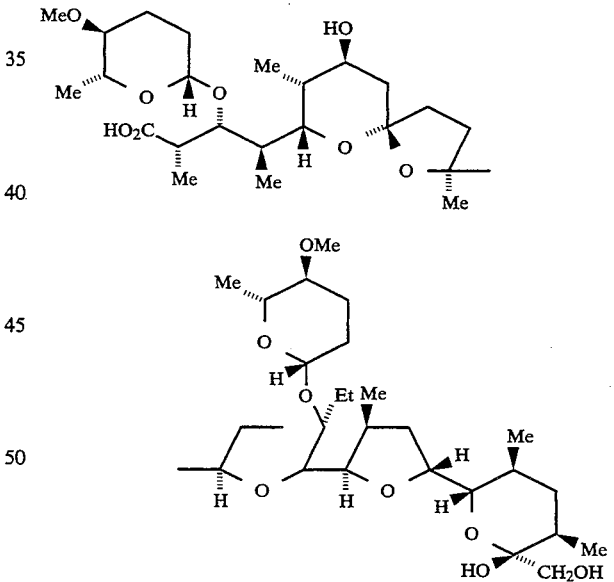

wherein Me=methyl and Et=ethyl in a recoverable quantity upon fermentation in an aqueous nutrient medium comprising assimilable sources of carbon and nitrogen.

2. The culture of claim 1 in freeze-dried form.

3. A biologically pure culture of Actinomadura sp. 53764.

* * * * *

UNITED STATES PATENT AND TRADEMARK OFFICE
CERTIFICATE OF CORRECTION

PATENT NO. : 5,403,738

DATED : April 4, 1995

INVENTOR(S) : John P. Dirlam, et al

It is certified that error appears in the above-indentified patent and that said Letters Patent is hereby corrected as shown below:

At column 1, lines 12-28,

" 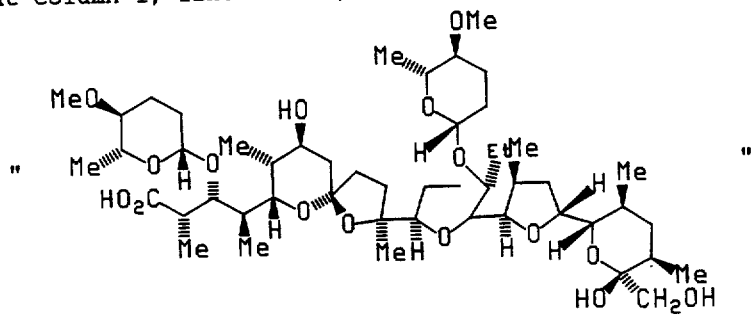 "

should read

-- 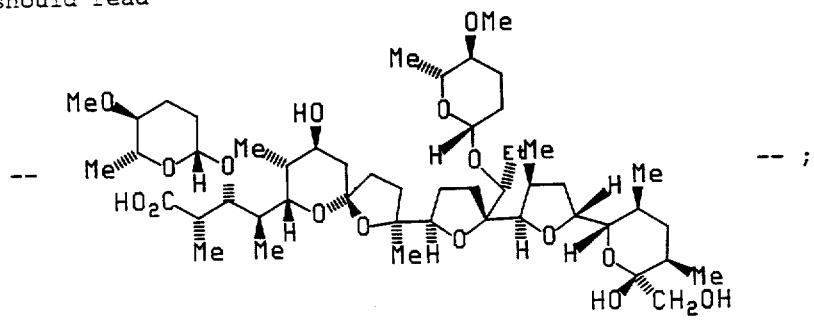 -- ;

UNITED STATES PATENT AND TRADEMARK OFFICE
CERTIFICATE OF CORRECTION

PATENT NO. : 5,403,738

DATED : April 4, 1995

INVENTOR(S) : John P. Dirlam, et al

It is certified that error appears in the above-indentified patent and that said Letters Patent is hereby corrected as shown below:

At column 12, lines 32-55,

" 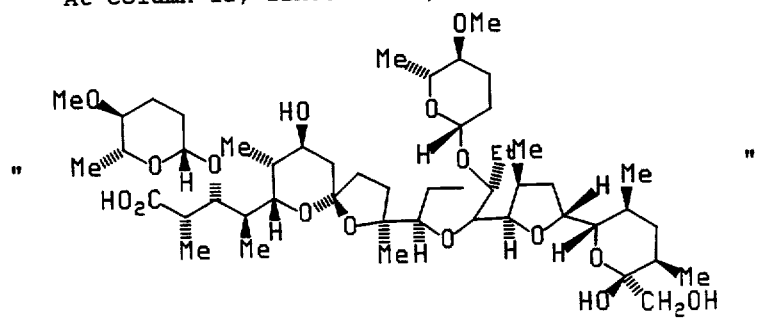 "

should read

-- 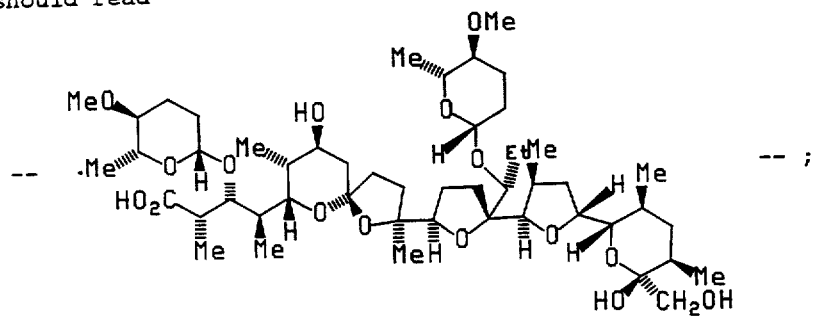 -- ;

Signed and Sealed this

Seventeenth Day of October, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,403,738
DATED : April 4, 1995
INVENTOR(S) : John P. Dirlam, et al Page 1 of 3

It is certified that error appears in the above-identified patent and that said Letters Patent is hereby corrected as shown below:

At column 1, lines 12-28,

" 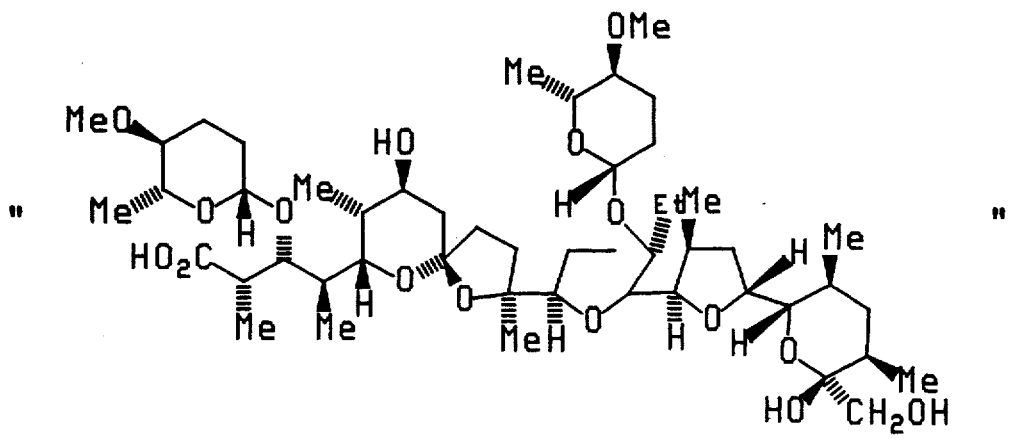 "

should read

-- 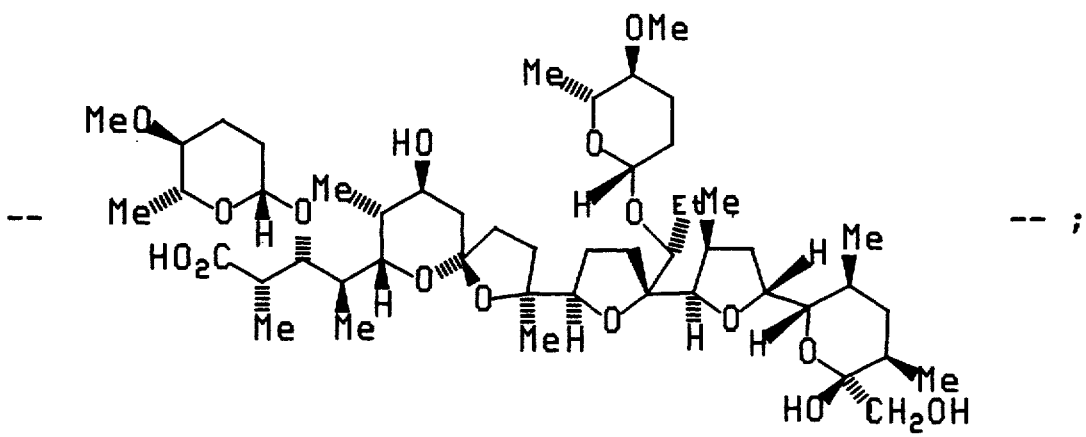 -- ;

UNITED STATES PATENT AND TRADEMARK OFFICE
CERTIFICATE OF CORRECTION

PATENT NO. : 5,403,738

DATED : April 4, 1995

INVENTOR(S) : John P. Dirlam, et al

It is certified that error appears in the above-identified patent and that said Letters Patent is hereby corrected as shown below:

At column 12, lines 32-55,

" 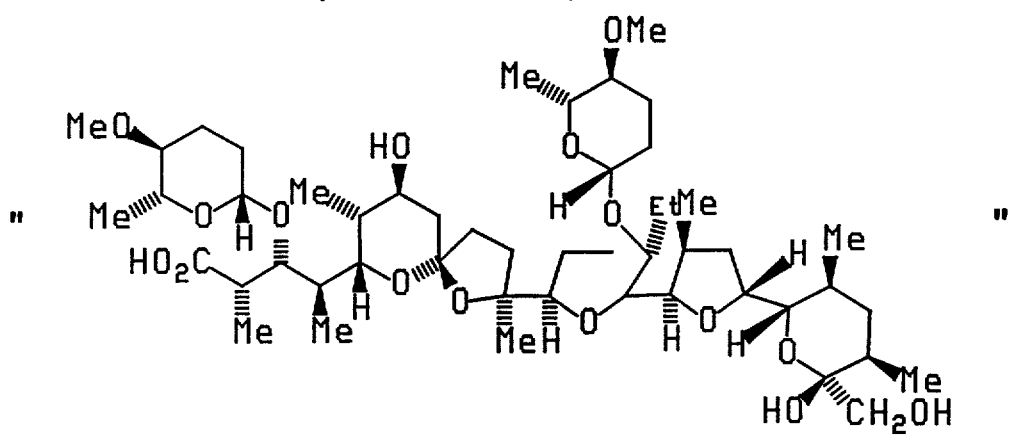 "

should read

UNITED STATES PATENT AND TRADEMARK OFFICE
CERTIFICATE OF CORRECTION

PATENT NO. : 5,403,738                         Page 3 of 3
DATED     : April 4, 1995
INVENTOR(S): John P. Dirlam, et al It is certified that error appears in the above-identified patent and that said Letters Patent is hereby corrected as shown below:

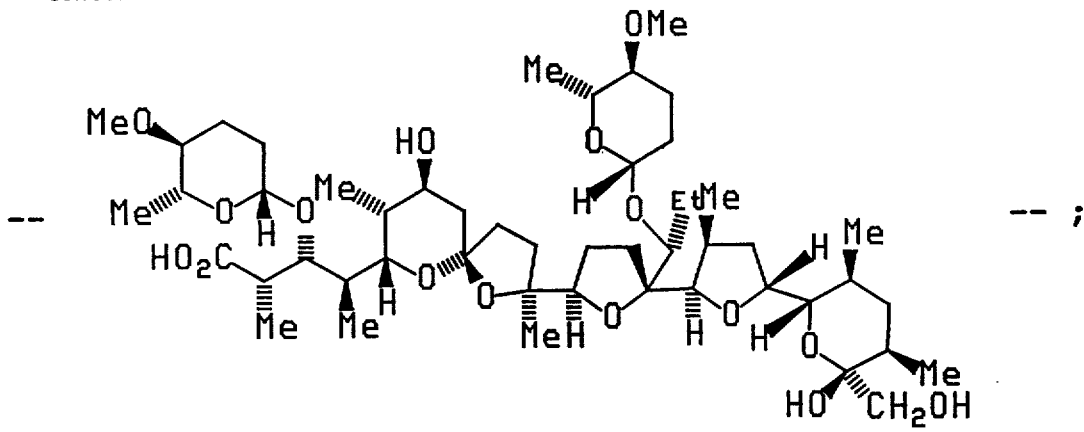

Signed and Sealed this

Twelfth Day of May, 1998

Attest:

BRUCE LEHMAN

*Attesting Officer*          Commissioner of Patents and Trademarks